(12) United States Patent
Masuda

(10) Patent No.: US 12,350,088 B2
(45) Date of Patent: Jul. 8, 2025

(54) RADIOGRAPHIC IMAGING APPARATUS, RADIOGRAPHIC IMAGING SYSTEM, AND CONTROL APPARATUS OF RADIOGRAPHIC IMAGING APPARATUS

(71) Applicant: CANON KABUSHIKI KAISHA, Tokyo (JP)

(72) Inventor: Rikuto Masuda, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 268 days.

(21) Appl. No.: 18/302,555

(22) Filed: Apr. 18, 2023

(65) Prior Publication Data
US 2023/0337999 A1    Oct. 26, 2023

(30) Foreign Application Priority Data

Apr. 25, 2022 (JP) .................................. 2022-071584

(51) Int. Cl.
*A61B 6/00* (2024.01)
*A61B 6/42* (2024.01)

(52) U.S. Cl.
CPC . *A61B 6/54* (2013.01); *A61B 6/42* (2013.01)

(58) Field of Classification Search
CPC ............ Y02E 60/10; H05G 1/10; H05G 1/08; H01M 10/4257; H01M 2200/00; H01M 10/4207; H01M 10/425; G06F 1/26; G06F 1/263; A61B 6/54; A61B 6/548; A61B 6/56
See application file for complete search history.

(56) References Cited

U.S. PATENT DOCUMENTS

2021/0196223 A1* 7/2021 Matsuda ................... G06T 5/70

FOREIGN PATENT DOCUMENTS

JP        2009198982 A        9/2009

* cited by examiner

*Primary Examiner* — Don K Wong
(74) *Attorney, Agent, or Firm* — Canon U.S.A., Inc. IP Division

(57) ABSTRACT

A radiographic imaging apparatus includes a charging unit that inputs current to a plurality of batteries to charge the plurality of batteries, and a current control unit that controls the current to be input by the charging unit to each of the plurality of batteries, wherein the current control unit determines based on a difference between a remaining charge of each of the plurality of batteries and a predetermined threshold, the current to be input by the charging unit to each of the plurality of batteries.

15 Claims, 12 Drawing Sheets

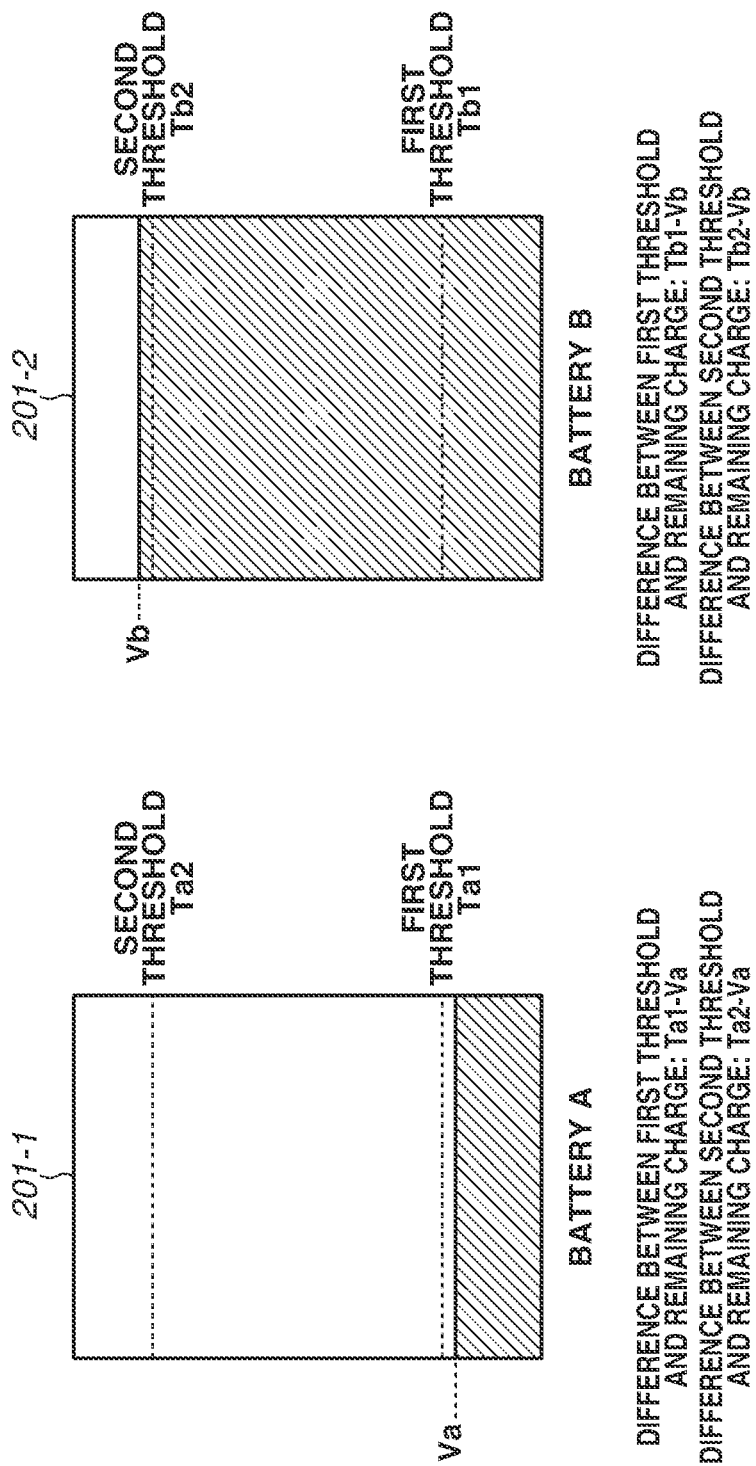

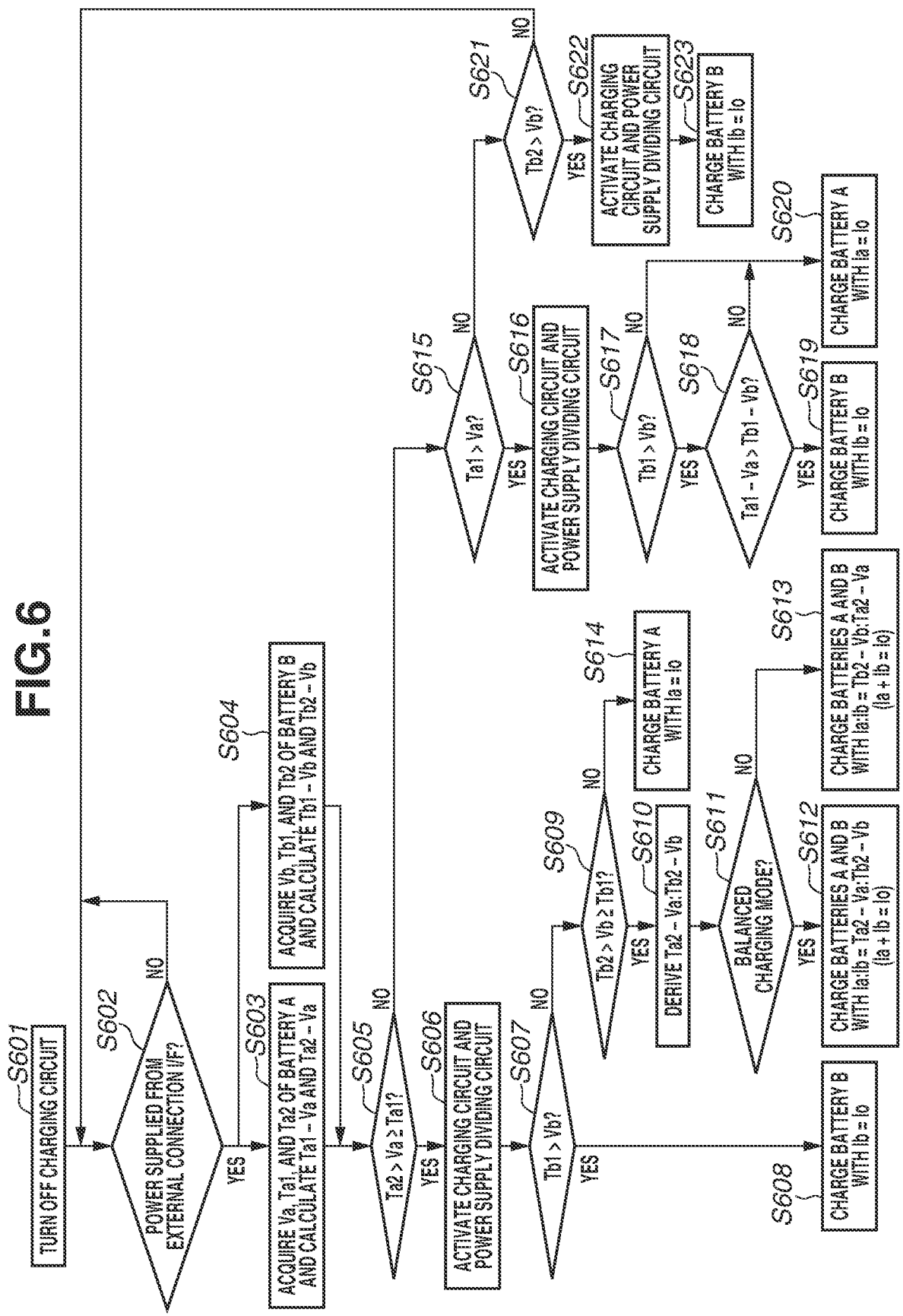

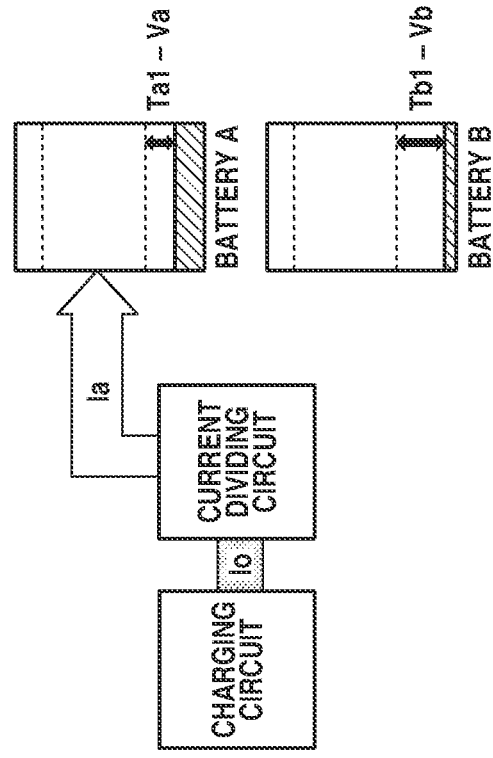
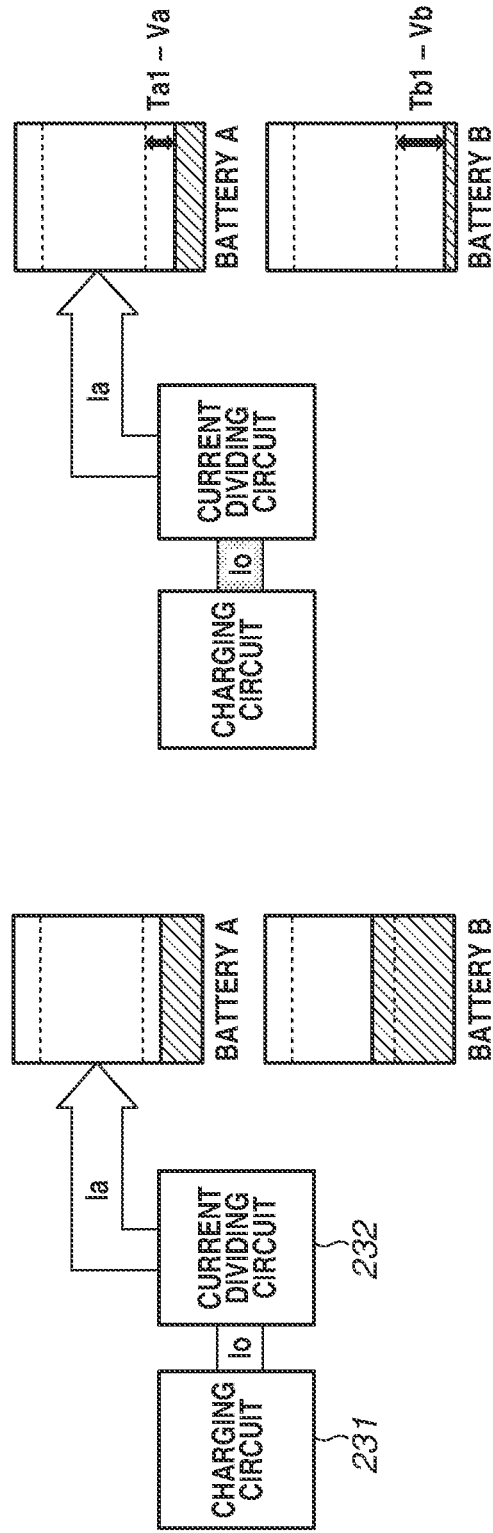
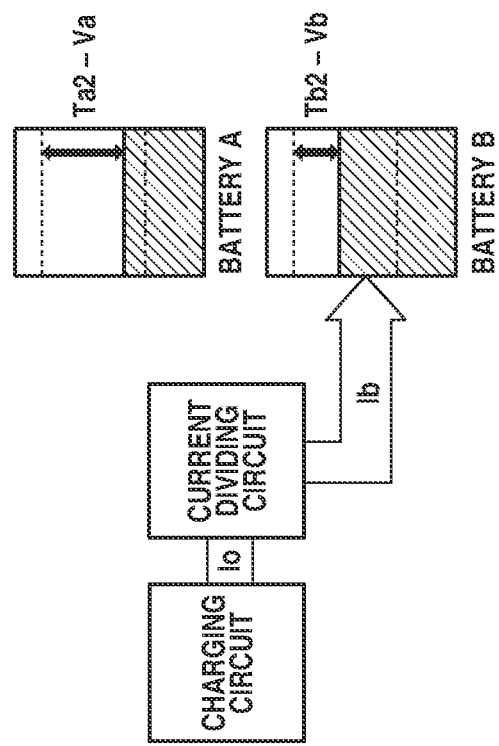

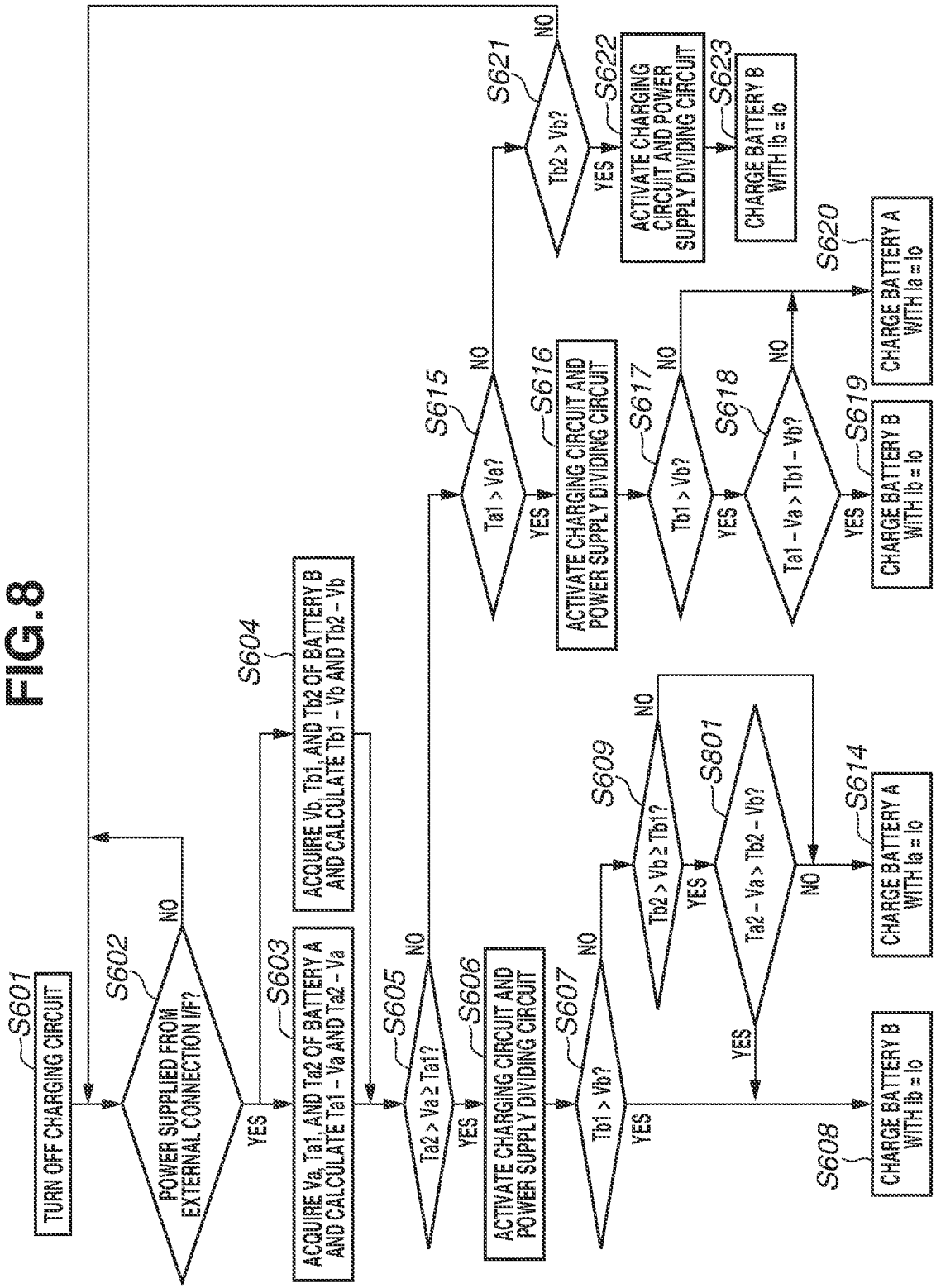

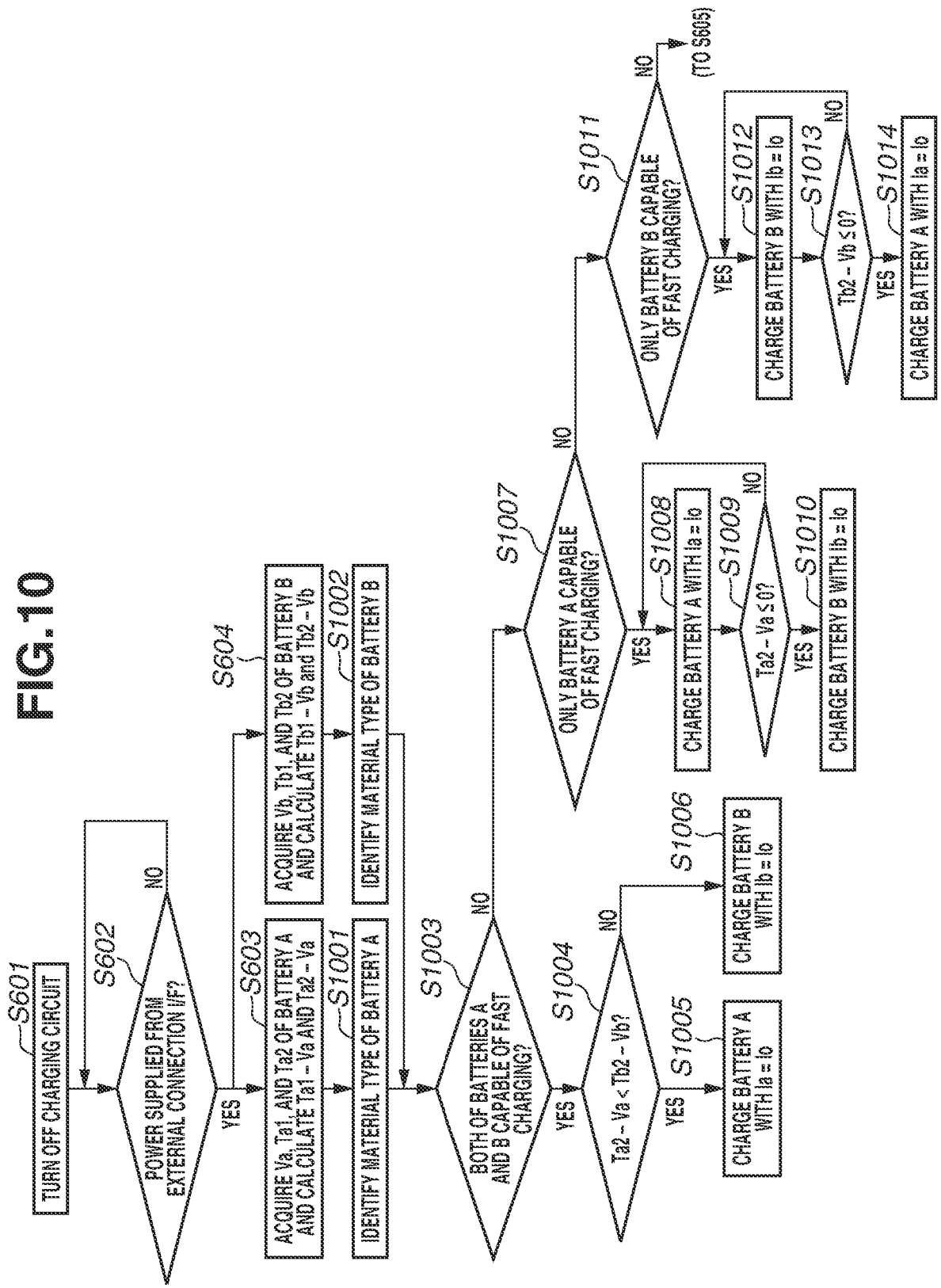

RADIOGRAPHIC IMAGING APPARATUS, RADIOGRAPHIC IMAGING SYSTEM, AND CONTROL APPARATUS OF RADIOGRAPHIC IMAGING APPARATUS

BACKGROUND

Field

The present disclosure relates to a radiographic imaging apparatus, a radiographic imaging system, and a control apparatus of the radiographic imaging apparatus.

Description of the Related Art

In recent years, radiographic imaging apparatuses using a flat panel detector (FPD) including a semiconductor material have been used. The FPD includes a two-dimensional matrix pixel array of a plurality of pixels that converts a radiation into an electrical signal, and converts the electrical signals from the pixel array into digital data and outputs one frame of digital radiographic image. This type of radiographic imaging apparatus is used in medical image diagnosis, as a digital imaging apparatus that performs still image capturing, such as general imaging, or performs moving image capturing, such as fluoroscopic imaging.

Wireless radiographic imaging apparatuses have been developed to improve handling of the radiographic imaging apparatuses. Because wireless radiographic imaging apparatuses are battery-operated, the number of images that can be captured with a single battery charge has an effect on usability of the radiographic imaging apparatus. Some radiographic imaging apparatuses are equipped with a plurality of batteries. Japanese Patent Application Laid-Open No. 2009-198982 discusses a radiographic imaging apparatus equipped with two or more batteries and a method for switching between batteries for a specific number of captured images.

SUMMARY

According to an aspect of the present disclosure, a radiographic imaging apparatus includes a charging unit configured to input current to a plurality of batteries to charge the plurality of batteries, and, a current control unit configured to control the current to be input by the charging unit to each of the plurality of batteries, wherein the current control unit determines, based on a difference between a remaining charge of each of the plurality of batteries and a predetermined threshold, the current to be input by the charging unit to each of the plurality of batteries.

Further features will become apparent from the following description of exemplary embodiments with reference to the attached drawings.

BRIEF DESCRIPTION OF THE DRAWINGS

FIG. 4 is a diagram illustrating the relationships between voltages and thresholds of batteries according to the first exemplary embodiment.

FIG. 6 is a flowchart of a charge operation according to the first exemplary embodiment.

FIGS. 7A to 7C are diagrams illustrating charge control of batteries according to a second exemplary embodiment.

FIG. 8 is a flowchart of a charge operation according to the second exemplary embodiment.

FIG. 10 is a flowchart of a charge operation according to a fourth exemplary embodiment.

DESCRIPTION OF THE EMBODIMENTS

Figure 1:
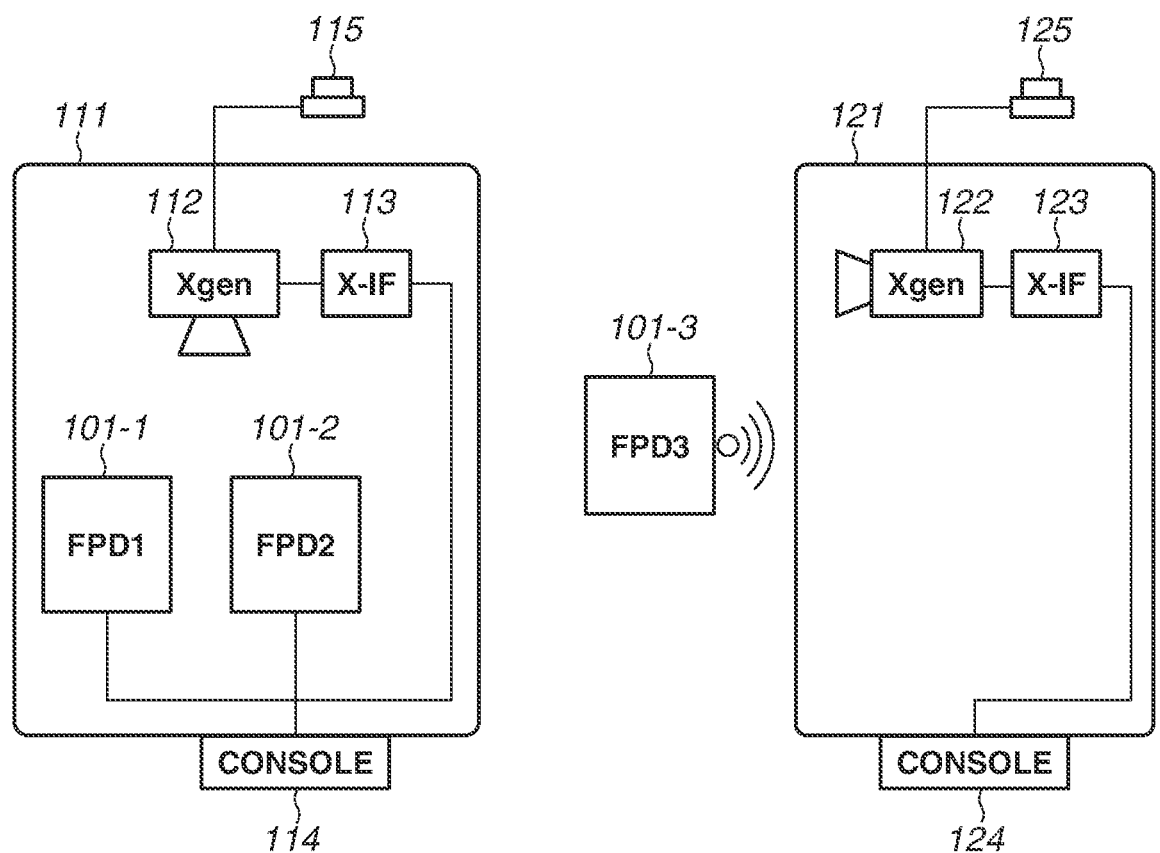
FIG. 1 is a diagram illustrating a radiographic imaging system according to a first exemplary embodiment.

The present exemplary embodiments are directed to shortening the downtime of a radiographic imaging apparatus. In a case of the radiographic imaging apparatus including a plurality of batteries, and when the plurality of batteries are charged at the same time, each of the batteries receives a portion of a charging current that is one out of the number of the batteries of the charging current output from a charging circuit, causing a decrease in the charging current input to each of the batteries. In this case, much time is consumed until the batteries are charged and the radiographic imaging apparatus becomes usable. Thus, a current to be input from a charging unit to each of the plurality of batteries is determined on the basis of the differences between remaining charges of the plurality of batteries and predetermined thresholds. This reduces the downtime of the radiographic imaging apparatus.

Hereinafter, specific examples of a radiographic imaging system according to the present exemplary embodiments will be described with reference to the accompanying drawings. In the following description and the drawings, components in common among the plurality of drawings are denoted with common reference numerals. Thus, the common components will be described with reference to the plurality of drawings, and the redundant descriptions of the components with the common reference numerals are omitted as appropriate.

Radial rays in the present exemplary embodiments can include α rays, β rays, and γ rays that are beams made of particles (including photons) emitted due to the decay of radial rays, and can also include beams with energy of the same degree, for example, X rays, particle rays, cosmic rays, and the like.

FIG. 1 is a diagram illustrating an example of a radiographic imaging system according to a first exemplary embodiment. The radiographic imaging system in the present exemplary embodiment is located, for example, in a radiographic imaging room 111 or on an instrument carriage 121.

The radiographic imaging apparatus 101 (101-1, 101-2, 101-3) in the following description is a portable FPD used in the radiographic imaging room 111 and in proximity to the instrument carriage 121 for radiographic imaging. The radiographic imaging apparatus 101 is operated with batteries or external power supplies.

First, a description will be provided of the radiographic imaging system being used in the radiographic imaging room 111. The radiographic imaging room 111 is provided with at least the radiographic imaging apparatus 101, a console 114 that controls the radiographic imaging apparatus 101, a radiation generation apparatus (Xgen) 112, a relay (X-IF) 113 that adjusts an operation timing of the radiographic imaging apparatus 101 and the radiation generation apparatus 112. As illustrated, a plurality of radiographic imaging apparatuses 101, i.e., radiographic imaging apparatuses 101-1 (FPD 1) and 101-2 (FPD 2), can be used in the same radiographic imaging system.

The radiation generation apparatus 112 includes an irradiation switch 115 that issues a radiation irradiation request. A connection between the console 114 and the radiographic imaging apparatus 101 is established via wireless local access network (LAN) communication under IEEE802.11 standard or via wired communication, such as, for example, Ethernet.

The wireless LAN communication can be infrastructure-mode communication in which any one of a wireless LAN access point (not illustrated), the radiographic imaging apparatus 101, and the console 114 performs an access-point operation to establish communication. Alternatively, the wireless LAN communication can be ad hoc-mode communication where the radiographic imaging apparatus 101 and the console 114 directly communicate with each other.

The console 114 includes a display unit that displays a state of the radiographic imaging apparatus 101 in a connectable mode. For example, whether the radiographic imaging apparatus 101 is in a standby state, whether the radiographic imaging apparatus 101 is completely prepared for image capturing, and the like.

A description will now be provided of the radiographic imaging system being used with the instrument carriage 121. The instrument carriage 121 is provided with a console 124 that controls the radiographic imaging apparatus 101-3 (FPD 3), a radiation generation apparatus (Xgen) 122, and a relay (X-IF) 123 that adjusts an operation timing of the radiographic imaging apparatus 101 and the radiation generation apparatus 122. The radiation generation apparatus 122 includes an irradiation switch 125 that issues a radiation irradiation request. Connection between the console 124 and the radiographic imaging apparatus 101 is established in a similar manner as described above with respect to the connection in the radiographic imaging room 111.

The console 114 and the console 124 can be stationary terminals, such as desktop personal computers (PCs), or can be built-in terminals that are incorporated in the instrument carriage 121 or the like. The console 114 and the console 124 can be mobile terminals, such as tablet PCs or smartphones of, for example, radiological technicians. Because mobile terminals are easy to carry, which is advantageous in emergency medication use at, for example, disaster sites, and in combination with mobile radiation generation apparatuses are also easy to carry.

Figure 2:
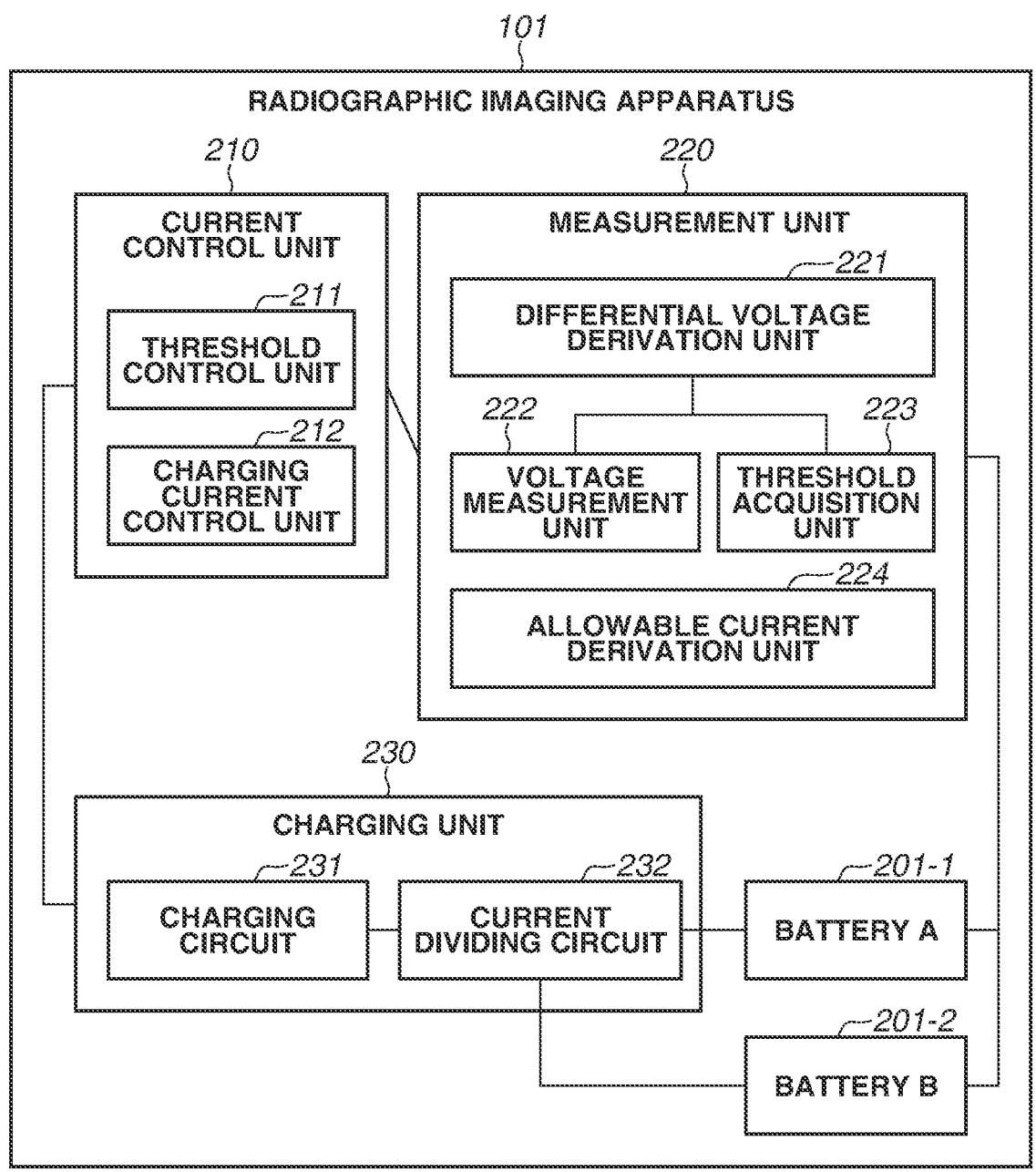
FIG. 2 is a block diagram illustrating an internal functional configuration of radiographic imaging apparatus according to the first exemplary embodiment.

FIG. 2 is a diagram illustrating internal functions of the radiographic imaging apparatus 101 according to the first exemplary embodiment. A configuration of the radiographic imaging apparatus 101 and operations of the elements included in the radiographic imaging apparatus 101 will be described with reference to FIG. 2.

The radiographic imaging apparatus 101 has a battery 201, a current control unit 210, a measurement unit 220, and a charging unit 230. In FIG. 2, the battery 201 includes two batteries 201-1 (battery A) and 201-2 (battery B). While, in the present exemplary embodiment, the radiographic imaging apparatus 101 includes two batteries, the number of batteries is not limited to two as long as the number of batteries is two or more. The type of battery materials that enable practice of the present embodiment. For example, the battery type can be lithium-ion battery, lithium-ion capacitor, electrical double layer capacitor, or the like, for example.

The current control unit 210 includes a threshold control unit 211 and a charging current control unit 212. The measurement unit 220 includes a differential voltage derivation unit 221, a voltage measurement unit 222, a threshold acquisition unit 223, and an allowable current derivation unit 224. The charging unit 230 includes a charging circuit 231 and a current dividing circuit 232 that divides or combines the current from the charging circuit 231. While FIG. 2 illustrates one charging circuit 231 and one current dividing circuit 232, two or more charging circuits 231 and two or more current dividing circuits 232 can be included in one radiographic imaging apparatus 101.

The threshold control unit 211 sets a predetermined threshold to change the charging current to the battery 201. The charging current control unit 212 sets a charging current to be input to the battery 201. The current value determined by the charging current control unit 212 is transmitted to the charging circuit 231 and the current dividing circuit 232, and the current to be input to the battery 201 is changed.

The voltage measurement unit 222 measures a voltage value (that is, the remaining charge) of the battery 201 mounted in the radiographic imaging apparatus 101. The threshold acquisition unit 223 acquires a value of the threshold for charge control set to the battery 201. The differential voltage derivation unit 221 derives the charging amount to be charged until the battery remaining charge reaches the threshold, from the values of the remaining charge and the threshold acquired by the voltage measurement unit 222 and the threshold acquisition unit 223. The allowable current derivation unit 224 acquires a value of the rated current of the battery 201 and transmits information on the value to the charging current control unit 212 to avoid flowing a charging current in excess of the allowable current of the battery 201.

The charging circuit 231 supplies the current to charge the battery 201 to the current dividing circuit 232. The charging circuit 231 can charge the battery 201 with a constant current or with a variable current with which the charging current can be changed in a case where the threshold is exceeded as described below. The current dividing circuit 232 performs a control to divide the current supplied from the charging circuit 231 between the batteries 201-1 and 201-2 based on the information received from the current control unit 210.

Figure 3:
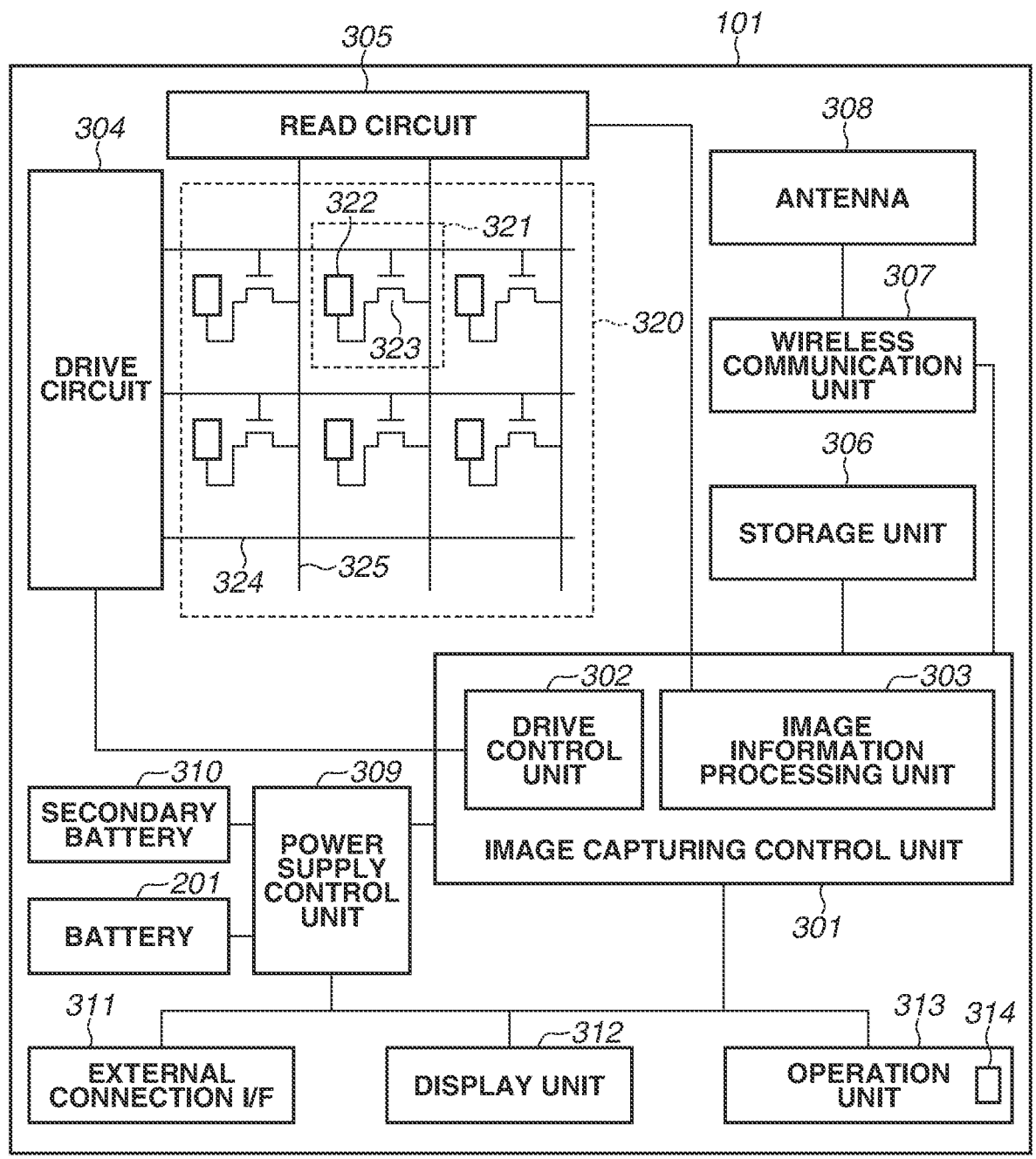
FIG. 3 is a block diagram illustrating a configuration relating to image generation in the radiation imaging apparatus according to the first exemplary embodiment.

FIG. 3 is a diagram illustrating a configuration of the radiation imaging apparatus 101 in the present exemplary embodiment.

An image capturing control unit 301 controls the operation of the radiographic imaging apparatus 101, and is provided with a drive control unit 302 and an image information processing unit 303.

The drive control unit 302 has a function of selecting (driving) switch elements arranged in a radiation detector 320. The radiation detector 320 is structured such that pixels 321, each having a photoelectric conversion element 322 formed of a semiconductor, are arranged in a two-dimensional matrix.

Each of the pixels 321 includes a switch element 323 and the photoelectric conversion element 322, and is covered with scintillator (not illustrated). The scintillator is excited by an emitted radiation and emits visible light. The photoelectric conversion element 322 converts the visible light into an electrical signal, and the pixels 321 convert the radiation into an electrical signal. The configuration of the pixel 321 is not limited to this. The pixel 321 can be a direct-conversion type pixel that directly converts the radiation into visible light.

At the time of driving the radiation detector 320, a drive circuit 304, in response to a control signal from the drive control unit 302, selects the row or column of pixels to be driven from among the plurality of pixels 321 included in the radiation detector 320.

The drive circuit 304 selects the pixels 321 in a certain row by a drive signal via drive wiring 324. The switch elements 323 of the pixels 321 in the selected row are turned on in sequence, and image signals (electric charges) accumulated in the photoelectric conversion elements 322 of the pixels 321 in the selected row are output to signal wiring 325 connected to the pixels 321.

The signal wiring 325 is connected to the image information processing unit 303 via a read circuit 305. The read circuit 305 has an amplifier input circuit (IC) and an analog-to-digital converter (ADC). The amplifier IC has the function of reading the image signals in sequence from the signal wiring 325 and amplifying the image signals. The ADC is a unit that converts the analog image signals read by the amplifier IC into digital signals. The digitally converted radiographic image data is input to the image information processing unit 303.

The image information processing unit 303 performs various processes on the input radiographic image data. Examples of these processes include, for example, defect correction to correct image defects, offset correction to correct offset data in the image, and noise reduction to reduce various noises. The image information processing unit 303 can perform part of the processes for diagnostic image creation, while some of the processes can be performed at the console 114 or 124.

The offset correction is to subtract unnecessary data, such as dark current components, generated during accumulation of radiographic images, and is performed by subtracting offset correction image data acquired without radiation irradiation from radiographic image data acquired with radiation irradiation. The gain correction is a kind of a process to correct image defects resulting from individual characteristic differences among the pixels arranged in the two-dimensional matrix. This process is performed to correct gain differences among the pixels, based on gain correction information obtained by uniform-dose irradiation in the absence of a subject.

A storage unit 306 stores the radiographic image data processed by the image information processing unit 303 and imaging information in association with each other. The storage unit 306 also stores imaging unit information. The storage unit 306 is a non-volatile memory, such as a flash memory.

In the present exemplary embodiment, the imaging information includes information on a patient that an image of has been captured, information on the person who captured the image, information on the imaged body portion, information on the imaging date and time, information, such as unique ID, for identification of the image, and the like. In a case where the radiographic imaging apparatus 101 performs image capturing in an imaging mode in which image capturing is started in response to detection of start of radiation irradiation, the imaging information also includes information used for the detection and determination of the radiation.

In the present exemplary embodiment, the imaging unit information includes the name of the imaging unit, the sensor size, the connection method (wireless or wired), and the like. The storage unit 306 can store one or more pieces of the imaging information in association with the radiographic image data. The storage unit 306 can also store defect information for use in image correction, the gain information for performing gain correction, or the operation history of the radiographic imaging apparatus 101.

A wireless communication unit 307 transmits the radiographic image data and the imaging information stored in the storage unit 306 to the console 114 or 124. The wireless communication unit 307 is connected to an antenna 308 and includes a circuit to transmit and receive radio waves via the antenna 308. The wireless communication unit 307 can transmit the radiographic image data processed by the image information processing unit 303 to a control device. Along with the transmission of the radiographic image data to the control device, the wireless communication unit 307 can store the radiographic image data in the storage unit 306. The transmission of the radiographic image data to the console 114 or 124 can be performed by wired communication via an external connection interface (I/F) (external connection I/F) 311.

A power supply control unit 309 controls a drive power source of the radiographic imaging apparatus. While not illustrated in FIG. 3, the power supply control unit 309 includes the current control unit 210. In response to supply of power from the battery 201, a secondary battery 310, and the external connection I/F 311, the power supply control unit 309 generates various power sources for driving of the radiographic imaging apparatus, and supplies power to the elements of the radiographic imaging apparatus 101. The power supply control unit 309 also controls charging of the battery 201 and the secondary battery 310.

A display unit 312 includes a display device that indicates the state of the radiographic imaging apparatus 101. The display device is a light-emitting device (LED) that indicates the state of the imaging unit (e.g., standby state or imaging-enabled state) and the charging amount of the battery. The display device is not limited to the LED, and can be, for example, a liquid crystal display or a display supporting touch operation.

An operation unit 313 includes a plurality of switches to receive an external input. The operation unit 313 includes an imaging-enabled state switch 314 that triggers transition to the imaging-enabled state.

Thresholds of the remaining charges set to the batteries 201-1 and 201-2 will now be described with reference to FIG. 4. A first threshold Ta1 is set to the battery 201-1. A first threshold Tb1 is set to the battery 201-2. The first thresholds Ta1 and Tb1 are limits of battery remaining charges with which at least one or a predetermined number of still images can be captured or a predetermined period of time of moving image capturing can be performed. The first thresholds Ta1 and Tb1 are desirably set within a range of 2 percent (%) to 10% of the battery capacity, with a more desired value of 5%.

The threshold setting to the battery 201 can be performed on the console 114 or the console 124. In another exemplary embodiment, the threshold setting can be performed on an apparatus other than the console 114 or 124 at, for example, the time the radiographic imaging apparatus 101 is shipped.

The predetermined number of images in still image capturing described above can be set by the user of the radiographic imaging apparatus 101 using the console 114 or the like. Different values can be set to each of the batteries 201-1 and 201-2. The predetermined period of time in moving image capturing can also be set by the user.

The predetermined numbers of images and the predetermined period of time can be set to default values that can be changed later. These values can also be automatically set based on the material or capacity of the batteries. The values of the predetermined numbers of images and the predetermined period of time can be individually set in advance based on the imaging mode (e.g., still image or moving image). These values can also be automatically changed in response to switching between imaging modes.

In the present exemplary embodiment, a second threshold Ta2 is set to the battery 201-1 and a second threshold Tb2 is set to the battery 201-2. The second thresholds Ta2 and Tb2 are values of limits beyond which the batteries 201-1 and 201-2 are overcharged.

The value of the limit beyond which a battery will be overcharged varies depending on the type of the battery. For example, the basic working voltage range of a lithium-ion battery is 3.0 volts (V) to 4.2 V, where charging a lithium-ion battery in excess of 4.2 V leads to overcharging. The value of overcharging (the second thresholds Ta2 and Tb2) is generally the value described above, but is not limited to 4.2 V. It can be less than 4.2 V, for example, for a situation where protecting the batteries 201-1 and 201-2 is desired.

In an example case illustrated in FIG. 4 where the remaining charge of the battery A is Va and the remaining charge of the battery B is Vb, the charging amount to reach the first threshold Ta1 of the battery A is Ta1−Va, and the charging amount to reach the second threshold Ta2 is Ta2−Va. Similarly, the charging amounts in the battery B are represented as Tb1−Vb and Tb−Vb.

Next, an image capturing operation based on a difference in the remaining charge between the batteries 201-1 and 201-2 will be described. Because the remaining charge Va falls under the first threshold Ta1 in the battery A, and the remaining charge Vb exceeds the first threshold Tb1 in the battery B, the image capturing operation is performed by using the battery B instead of the battery A. In a case of charging the batteries 201-1 and 201-2, since the battery B has the remaining charge Vb exceeding the second threshold Tb2, the battery B is not charged. As described above, the batteries 201-1 and 201-2 have the first thresholds Ta1 and Tb1 beyond which the image capturing operation is enabled and the second thresholds Ta2 and Tb2 set to prevent overcharging.

Figure 5A:
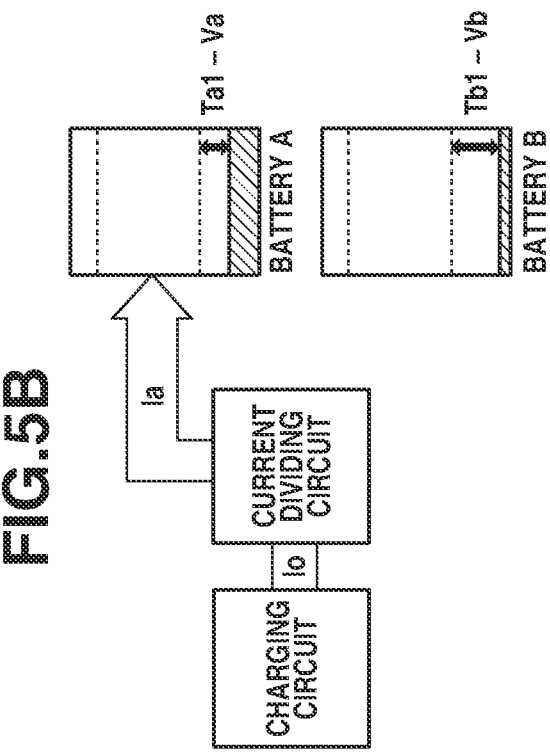
FIGS. 5A to 5D are diagrams illustrating charge control of the batteries according to the first exemplary embodiment.

Control of charging currents based on a result of comparison between the battery remaining charges and the thresholds will be described with reference to FIGS. 5A to 5D. First, a description will be provided of a case where the remaining charge Va of the battery A falls under the first threshold Ta1 and the remaining charge Vb of the battery B exceeds the first threshold Tb1 (FIG. 5A).

In this case, the current dividing circuit 232 performs control such that all output current Io output by the charging circuit 231 becomes charging current Ia that flows to the battery A (Io=Ia).

In a case where the remaining charge Vb of the battery B falls under the second threshold Tb2, the battery B can be charged, and thus is in general to be charged with input of the charging current. In this case, however, the remaining charge of the battery B is still at an operable level, and thus a higher priority is placed on immediate charging of the battery A.

Figure 5B:
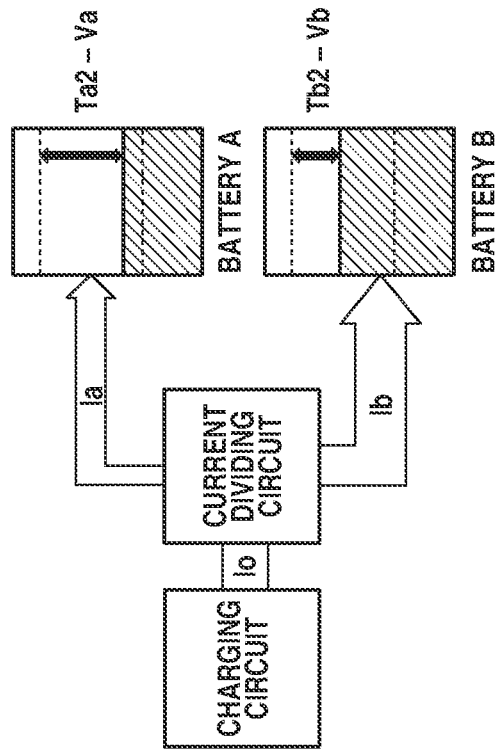

A description will now be provided of a case where both the remaining charges Va and Vb of the batteries A and B fall under the first thresholds Ta1 and Tb1 (FIG. 5B). In this case, since the battery A and the battery B both fall under the first thresholds Ta1 and Tb1, respectively, charging both of the batteries A and B are given priority. However, if both of the batteries are charged at the same time, the current is divided at a ratio of 1:1, causing a decrease in the charging speed.

In this case, to bring the battery remaining charges Va and Vb to reach the first thresholds Ta1 and Tb1 in the shortest time, charging the battery with a smaller difference from the first threshold between Ta1−Va and Tb1−Vb is given priority. That is, the charging amount Ta1−Va to reach the first threshold Ta1 of the battery A and the charging amount Tb1−Vb to reach the first threshold Tb1 of the battery B are compared, and the battery with a smaller charging amount is charged. This enables charging the battery at a speed twice as high than in the case of charging with the current divided at a ratio of 1:1. Thus, charging the battery closer to the first threshold enables the remaining charge to reach the operation-enabled level in the shortest time.

Figure 5C:
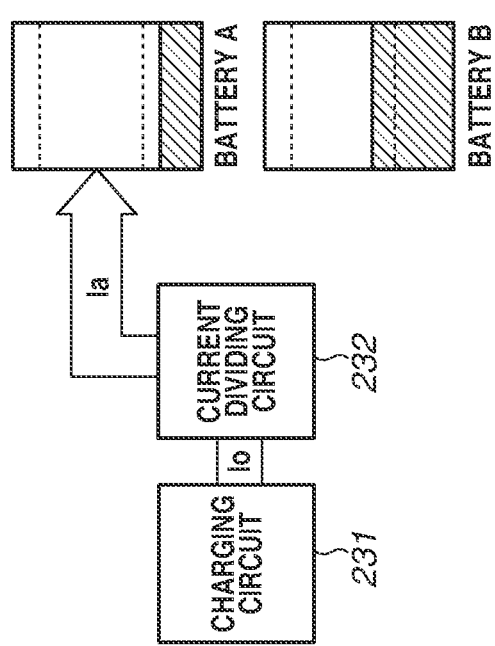
Figure 5D:
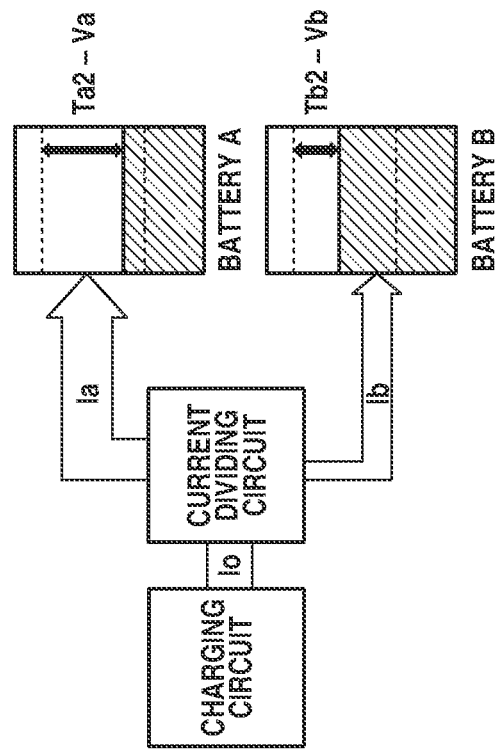
Figure 9B:
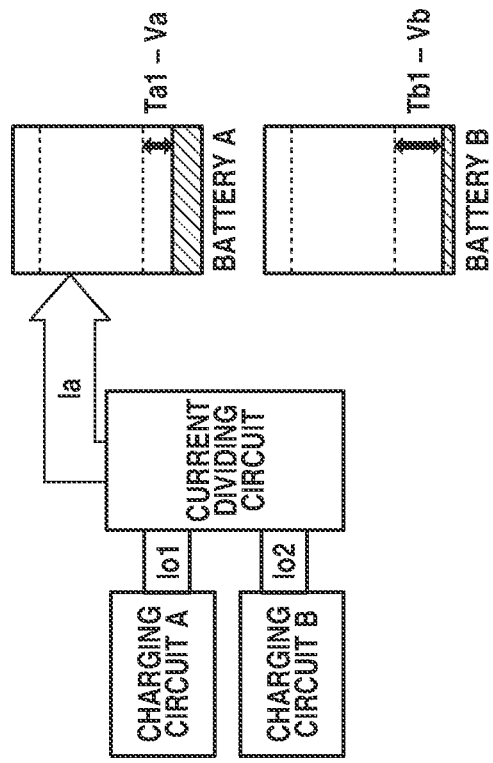
FIGS. 9A to 9D are diagrams illustrating charge control of batteries according to a third exemplary embodiment.
Figure 9D:
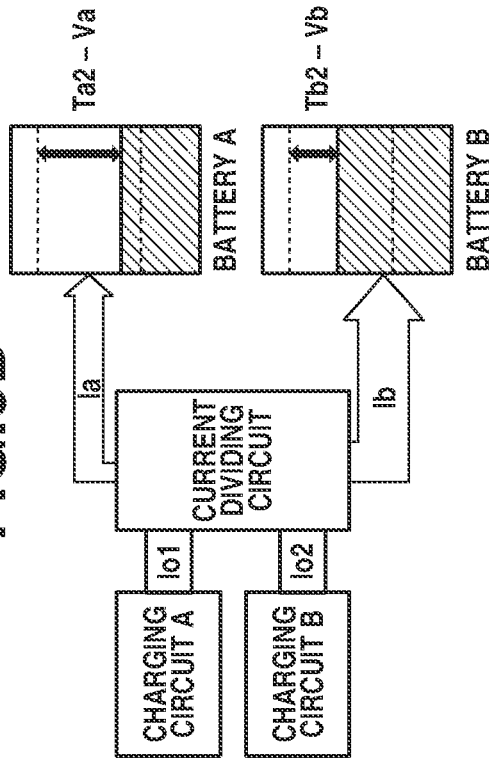
Figure 9A:
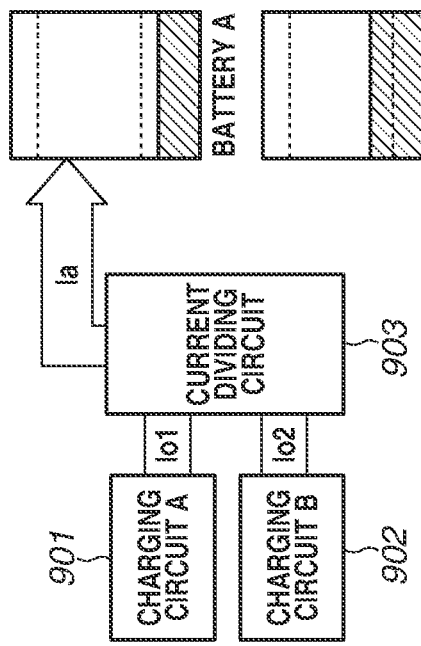
Figure 9C:
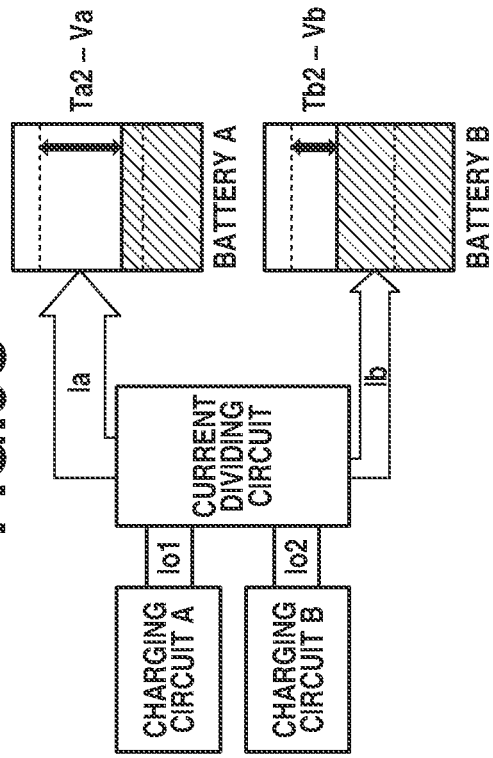

Next, a description will be provided of a case where the remaining charges Va and Vb of the batteries A and B both exceed the first thresholds Ta1 and Tb1 and fall under the second thresholds Ta2 and Tb2 (FIGS. 5C and 5D).

In this case, since both of the batteries A and B have the remaining charges Va and Vb at the operable level, there is no priority between the batteries A and B to perform charging. Thus, charging the battery with a lower remaining charge (FIG. 5C) or charging the battery with a higher remaining charge is given priority (FIG. 5D). According to the charging method illustrated in FIG. 5C, in order to bring the batteries A and B to the same remaining charges, the charging is controlled such that the batteries A and B are charged while a balance between the batteries A and B are maintained. According to the charging method illustrated in FIG. 5D, the charging is controlled such that one of the batteries A or B reaches the second threshold while charging both of the batteries A and B to bring the one battery into the fully charged state.

In the case of using the charging method illustrated in FIG. 5D, the fully charged battery can be replaced with the battery having a low remaining charge and the battery having a low remaining charge can be charged at a high speed. In the charging methods illustrated in FIGS. 5C and 5D, the ratio between the charging amount Ta2−Va to reach the second threshold Ta2 of the battery A and the charging amount Tb2−Vb to reach the second threshold Tb2 of the battery B is derived, and the battery A and the battery B are charged based on the ratio.

In the example of FIG. 5C, in a case where (Ta2−Va):(Tb2−Vb)=1:2, the batteries A and B are charged with the charging current divided at Ia:Ib=1:2 (balanced charging mode). In the charging method illustrated in FIG. 5D, charging is performed under the concept opposite to the charging method illustrated in FIG. 5C. That is, in a case where (Ta2−Va):(Tb2−Vb)=1:2, the batteries A and B are charged with the charging current divided at Ia:Ib=2:1 (priority charging mode). The total of Ia and Ib is Io.

A charging method to be used can be set from among the charging methods illustrated in FIGS. 5C and 5D by the user using the console 114 or the like. Alternatively, the current control unit 210 can automatically determine the charging method based on the time zone of charging. For example, the charging method illustrated in FIG. 5C is selected for the nighttime, during which sufficient charging time can be secured, and the charging method illustrated in FIG. 5D is selected for the daytime, during which rapid charging is desirable.

In the charging method illustrated in FIG. 5C, in a case where the battery A with a lower remaining charge is given a priority to be charged and then the remaining charge Va exceeds the remaining charge Vb of the battery B, the remaining charges Va and Vb can be compared with the second thresholds Ta2 and Tb2, i.e., comparing Ta2−Va and Tb2−Vb, and the allocation of the charging current can be changed. Once the allocation of the charging current is determined, the allocation can be maintained until the target threshold is reached.

The foregoing are methods of charge control by the comparison between the battery remaining charges Va and Vb and the thresholds Ta1, Tb1, Ta2, and Tb2. Under such control, when a battery with a low remaining charge is to be charged, the battery can be charged as rapidly as possible, and when a battery has an enough remaining charge, the charging current is decreased to suppress degradation of the battery.

FIG. 6 is a flowchart of an operation according to the present exemplary embodiment.

First, in step S601, the process is started by turning off the charging circuit 231 to prevent power consumption. Next, in step S602, determination of whether power is supplied from the external connection I/F 311 is performed. In a case where no power is supplied (NO in step S602), the processing in step S602 is repeated.

In a case where power is supplied (YES in step S602), the processing proceeds to step S603 for the battery A, and proceeds to step S604 for the battery B. In the present exemplary embodiment, a process of deriving differences between the remaining charge Va of the battery A and the thresholds Ta1 and Ta2 and a process of deriving differences between the remaining charge Vb of the battery B and the thresholds Tb1 and Tb2 (Ta1−Va and Ta2−Va for the battery A, and Tb1−Vb and Tb2−Vb for the battery B) are performed in parallel.

After the processing for the batteries A and B, in step S605, determination of whether the remaining charge Va of the battery A is greater than or equal to the first threshold Ta1 and is less than the second threshold Ta2 (Ta2>Va≥Ta1) is performed for comparison between the battery remaining charges by the derived differences.

In a case where the remaining charge Va of the battery A is greater than or equal to the first threshold Ta1 and is less than the second threshold Ta2 (YES in step S605), charging is to be performed as initiated in step S606. In step S606, the charging circuit 231 is activated. Then, in step S607, determination of whether the remaining charge Vb of the battery B is less than the first threshold Tb1 (Tb1>Vb) is performed. In a case where the remaining charge Vb of the battery B is less than the first threshold Tb1 (YES in step S607), the processing proceeds to step S608. In step S608, all the current Io output from the charging circuit 231 is input to the battery B.

In a case where the remaining charge Vb of the battery B is greater than or equal to than the first threshold Tb1 (NO in step S607), the processing proceeds to step S609. In step S609, determination of whether the remaining charge Vb of the battery B is greater than or equal to the first threshold Tb1 and is less than the second threshold Tb2 (Tb2>Vb≥Tb1) is performed. In a case where it is determined that the remaining charge Vb is Tb2>Vb≥Tb1 (YES in step S609), the processing proceeds to step S610. In step S610, the ratio of the differences between the remaining charges Va and Vb of the batteries A and B and the second thresholds Ta2 and Tb2 is derived by Ta2−Va:Tb2−Vb. In step S611, determination of whether the charging mode to be applied is a mode for a case in which both the remaining charges Va and Vb of the batteries A and B are greater than or equal to the first thresholds Ta1 and Tb1 and are less than the second thresholds Ta2 and Tb2, i.e., the balanced charging mode is performed.

In a case where the charging mode to be applied is the balanced charging mode (YES in step S611), the processing proceeds to step S612. In step S612, the batteries A and B are charged with the current Io divided at Ta2−Va:Tb2−Vb=Ia:Ib. In a case where the charging mode to be applied is not the balanced charging mode but the priority charging mode (NO in step S611), the processing proceeds to step S613. In step S613, the batteries A and B are charged with the current Io divided at Ta2−Va:Tb2−Vb=Ia:Ib. In a case where it is determined that the remaining charge Vb is not Tb2>Vb≥Tb1 (NO in step S609), the battery B does not need to be charged, and in step S614, only the battery A is charged.

Next, a description will be provided of a case in where it is not determined in step S605 that the remaining charge Va of the battery A is greater than or equal to the first threshold Ta1 and is less than the second threshold Ta2 (NO in step S605), and it is determined that the remaining charge Va of the battery A is less than the first threshold Ta1 (YES in step S615). In step S616, as in step S606, the charging circuit 231 is activated first. Next, in step S617, determination of whether the remaining charge Vb of the battery B is smaller than the first threshold Tb1 is performed.

In a case where the remaining charge Vb of the battery B is less than the first threshold Tb1 (YES in step S617), the processing proceeds to step S618. In step S618, the difference between the first threshold Ta1 and the remaining charge Va of the battery A (Ta1−Va) and the difference between the first threshold Tb1 and remaining charge Vb of the battery B (Tb1−Vb) are compared. In a case where the difference between the first threshold Ta1 and the remaining charge Va of the battery A is greater than the difference between the first threshold Tb1 and the remaining charge Vb (YES in step S618), the processing proceeds to step S619. In step S619, the battery B is charged. In a case where the difference between the first threshold Tb1 and remaining charge Vb of the battery B is greater than the difference between the first threshold Ta1 and the remaining charge Va (NO in step S618), the processing proceeds to step S620. In step S620, the battery A is charged. In a case where it is determined in step S617 that the remaining charge Vb of the battery B is greater than or equal to the first threshold Tb1 (NO in step S617), the remaining charge Va of the battery A is less than the first threshold Ta1, and charging the battery A is given priority. Thus, in step S620, the battery A is charged with Ia=Io.

In a case where it is determined in step S615 that the remaining charge Va of the battery A is greater than or equal to the first threshold Ta1 (NO in step S615), the process proceeds to step S621. In this processing, since the remaining charge Va of the battery A is greater than or equal to the second threshold Ta2, the battery A is not charged. In step S621, determination of whether the remaining charge Vb of the battery B is greater than the second threshold Tb2 is performed. In a case where the remaining charge Vb is less than the second threshold Tb2 (YES in step S621), the processing proceeds to step S622. In step S622, the charging circuit is activated, and then in step S623, the battery B is charged with Ib=Io. In a case where it is determined that the remaining charge Vb of the battery B is greater than or equal to the second threshold Tb2 (NO in step S621), both the remaining charges Va and Vb of the batteries A and B are greater than or equal to the second thresholds Ta2 and Tb2. Thus, the processing returns to step S602 without charging the batteries A and B.

While, in the present exemplary embodiment, two batteries are provided as an example, the number of batteries can be greater than two. While, in the above-described processing procedure, the remaining charge Va of the battery A is first determined and then the remaining charge Vb of the battery B is determined, the order of determination is not limited to this. While, in the flowchart of FIG. 6, determination on the current derived by the allowable current derivation unit 224 is not described, determination of whether the charging current to each of the batteries A and B does not exceed the allowable current is performed at the time of current input to each of the batteries.

According to the present exemplary embodiment, the charging current to be input to the batteries A and B can be appropriately controlled. This enables shortening the time until the radiographic imaging apparatus becomes usable.

Control of charging currents in a second exemplary embodiment will be described with reference to FIGS. 7A to 7C. Descriptions of parts similar to those in the first exemplary embodiment are omitted herein.

The present exemplary embodiment is different from the first exemplary embodiment in charge control in a case where remaining charges Va and Vb of batteries A and B are greater than or equal to the first thresholds and are less than or equal to the second thresholds.

Referring to FIGS. 7A to 7C, charging methods illustrated in FIGS. 7A and 7B are similar to the charging methods illustrated in FIGS. 5A and 5B. A difference is in charge control is illustrated in FIG. 7C. Referring to FIG. 7C, Ta2−Va and Tb2−Vb are compared, charging the battery with a smaller value is given priority, and the other battery is not charged. This control enables one battery to be charged quickly to full capacity, and consequently, the fully-charged battery can be replaced with an empty battery to charge the empty battery.

FIG. 8 is a flowchart of a charge operation according to the present exemplary embodiment. The differences from the flowchart of FIG. 6 are in the steps performed in a case where the remaining charges Va and Vb of the batteries A and B are greater than or equal to the first thresholds Ta1 and Tb1 and are less than or equal to the second thresholds Ta2 and Tb2. Thus, only the corresponding steps from FIG. 6 (S609, S608, and S614) will be discussed the descriptions of the remaining steps are omitted herein.

As in the processing illustrated in FIG. 6, in step S609, determination of whether the remaining charge Vb of the battery B satisfies Tb2>Vb≥Tb1 is performed. In a case where it is determined that Tb2>Vb≥Tb1 is satisfied (YES in step S609), the processing proceeds to step S801. In step S801, determination of whether the remaining charge Vb of the battery B is closer to the second threshold than the remaining charge Va of the battery A is performed. In a case where the remaining charge Vb of the battery B is closer to the second threshold than the remaining charge Va of the battery A (YES in step S801), the processing proceeds to step S608. In a case where the remaining charge Vb of the battery B is not closer to the second threshold than the remaining charge Va of the battery A (NO in step S801), the processing proceeds to step S614. The battery closer to the second threshold (the battery with a smaller value of Ta2−Va or Tb2−Vb) is charged in step S608 or step S614.

According to the present exemplary embodiment, in a case where the remaining charge is greater than or equal to the first threshold and is less than the second threshold, charging the battery with the remaining charge closer to the second threshold is given priority to be fully charged. The present exemplary embodiment is useful in the configuration of the batteries that are easily replaceable, and it is possible to increase the number of fully charged batteries and quickly prepare the replaceable fully charged batteries.

Control of charging currents in a third exemplary embodiment will be described with reference to FIGS. 9A to 9D. Descriptions of parts similar to those in the first exemplary embodiment are omitted herein.

The present exemplary embodiment is different from the first exemplary embodiment in the number of charging circuits. In the first exemplary embodiment, one charging circuit is provided for a plurality of batteries. In the present exemplary embodiment, the same number of charging circuits as number of batteries are provided. A method for controlling charging current based on the differences between the remaining charges Va and Vb and the thresholds Ta1, Tb1, Ta2, and Tb2 of batteries A and B is similar to that in the first exemplary embodiment, and thus the redundant descriptions are omitted herein.

Differences of the present exemplary embodiment from the first exemplary embodiment are that the total of currents output from charging circuits A 901 and B 902 is Io1+Io2, and that output currents from the plurality of charging circuits A 901 and B 902 can be input to a current dividing circuit 903.

The currents output from the charging circuits A 901 and B 902 are input to the current dividing circuit 903, and the current in the current dividing circuit 903 is divided into the number of the batteries. As in the first exemplary embodiment, the currents to be input to the batteries are controlled to avoid exceeding the allowable current. For example, referring to FIG. 9A, a charging current Ia input to the battery A is Ia=Io1+Io2 at maximum, but in a case where an allowable current Ia(limit) of the battery A is Ia(limit)<Io1+Io, the charging current Ta is controlled by the current dividing circuit 903 to avoid exceeding the allowable current Ia(limit).

At the time of acquisition of an image by a radiographic imaging apparatus, unnecessary artifacts can occur in the image due to thermal distribution. In the present exemplary embodiment, since a plurality of charging circuits is provided, heat generation is suppressed even if the charging current becomes large. Thus, it is possible to suppress the occurrence of artifacts by suppressing heat generation while securing the charging current, as compared with the case where one charging circuit is provided.

Control of charging currents in a fourth exemplary embodiment will be described with reference to FIG. 10.

In the present exemplary embodiment, control is performed such that the types of batteries are identified and the battery to be given a priority to be charged is determined. In the first exemplary embodiment, the charging current is controlled based on comparison of the differences between the thresholds and remaining charges regardless of the types of batteries. In the present exemplary embodiment, control is performed such that charging a battery using, for example, a lithium-ion capacitor, which increases the charging current is given priority.

A processing procedure of the present exemplary embodiment will be described with reference to FIG. 10. The present exemplary embodiment is different from the first exemplary embodiment in that some steps are added to the step of comparing the differences between the remaining charges and the thresholds of batteries A and B (step S605 in FIG. 6).

In steps S603 and S604, the differences between the voltages and thresholds of the batteries are acquired as described in FIG. 6, and then, in steps S1001 and S1002, the materials of the batteries A and B are identified. The function of identifying the materials of the batteries A and B can be performed by any of the components included in the measurement unit 220 or an identification unit separately disposed in a radiographic imaging apparatus 101.

Next, in step S1003, determination of whether the batteries A and B are capable of fast charging is performed. The determination is made based on the battery materials identified in steps S1001 and S1002.

In a case where both of the batteries A and B are capable of fast charging (YES in step S1003), the processing proceeds to step S1004. In step S1004, determination of whether the remaining charge Va of the battery A is closer to the second threshold than the remaining charge Vb of the battery B. In a case where remaining charge Va of the battery A is closer to the second threshold than the remaining charge Vb of the battery B (YES in step S1004), the processing proceeds to step S1005. In a case where the remaining charge Va of the battery A is not closer to the second threshold than the remaining charge Vb of the battery B (NO in step S1004), the processing proceeds to step S1006. The battery with the remaining charge closer to the second threshold is charged in step S1005 or step S1006.

In a case where both of the batteries A and B are not capable of fast charging (NO in step S1003), the processing proceeds to step S107. In step S1007, if it is determined that only the battery A is capable of fast charging (YES in step S1007), the processing proceeds to step S1008. In step S1008, the battery A is charged. Next, in step S1009, in a case where the battery A is fully charged (YES in step S1009), the processing proceeds to step S1010, where the battery B is charged.

In a case where both of the batteries A and B are not capable of fast charging (NO in step S1007), the processing proceeds to step S1011. In step S1011, if it is determined that only the battery B is capable of fast charging (YES in step S1011), then in step S1012, the battery B is charged. In a case where the battery B is fully charged (YES in step S1013), in step S1014, the battery A is charged. In a case where the battery B is not fully charged (NO in step S1013), the processing returns to step S1012. In a case where neither of the batteries A and B is capable of fast charging (NO in step S1011), the processing proceeds to step S605, which is described above with respect to FIG. 6.

In the present exemplary embodiment, charging a plurality of batteries can be efficiently performed in a case where the plurality of batteries include a battery made of a material capable of fast charging.

Figure 11:
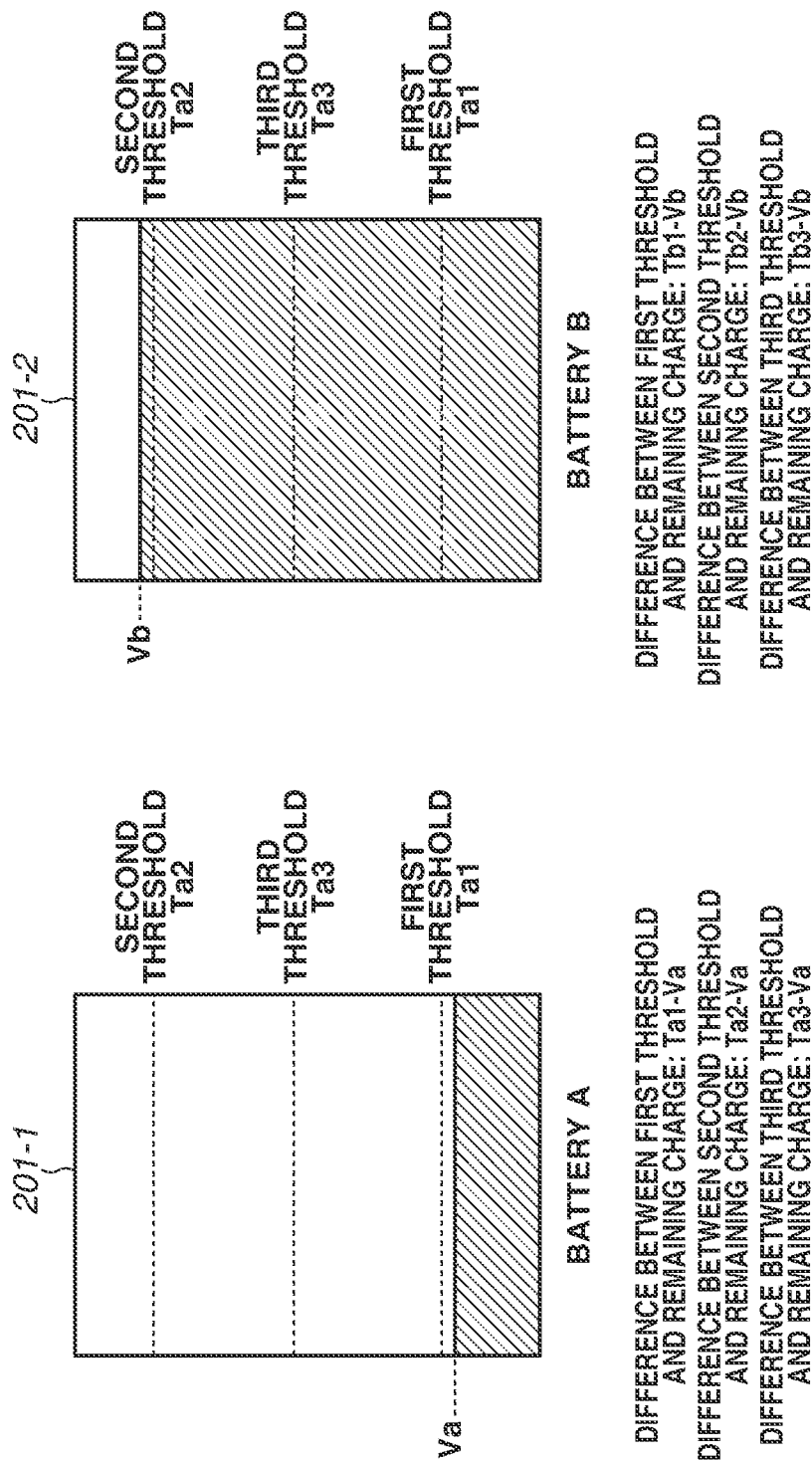
FIG. 11 is a diagram illustrating the relationships between voltages and thresholds of batteries according to a fifth exemplary embodiment.

Control of charging currents in a fifth exemplary embodiment will be described with reference to FIG. 11. In the present exemplary embodiment, in addition to the first thresholds and the second thresholds as described in the first exemplary embodiment, third thresholds are provided in the charging control of the present exemplary embodiment.

In the first exemplary embodiment, the first thresholds Ta1 and Tb1 at the operable limit of the radiographic imaging apparatus 101 and the second thresholds Ta2 and Tb2 at the overcharging limit are set. In the present exemplary embodiment, third thresholds Ta3 and Tb3 are also set. The magnitude relationship among the thresholds is the second threshold T2>the third threshold T3>the first threshold T1. The third thresholds Ta3 and Tb3 are set at values with which batteries are charged to the level in which the radiographic imaging apparatus 101 is sufficiently operable. The third thresholds can be set by the user or can be set to unique values for each respective battery.

Figure 12B:
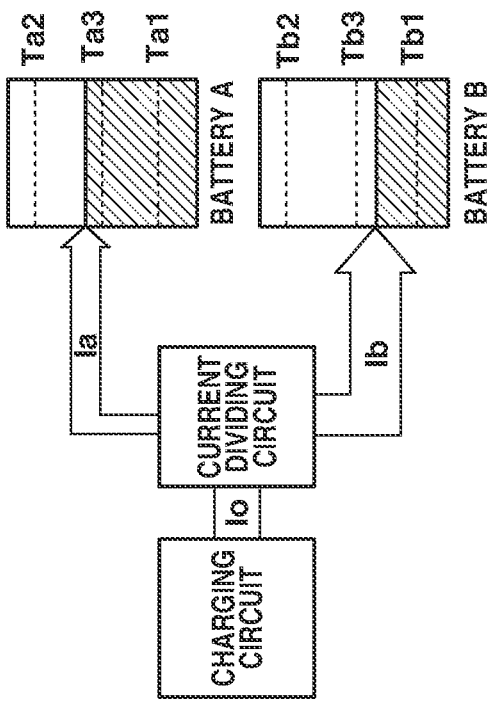
FIGS. 12A and 12B are diagrams illustrating charge control of the batteries according to the fifth exemplary embodiment.

The third thresholds can be used as thresholds where, for example, the current in the first exemplary embodiment is to be divided. In this case, as illustrated in FIGS. 12A and 12B, control is performed such that the ratio of charging currents is changed when the remaining charge exceeds the third threshold.

Figure 12A:
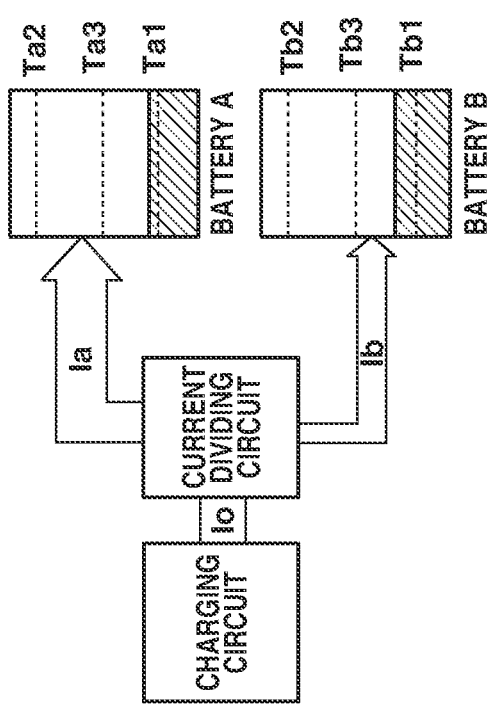

In a case illustrated in FIG. 12A, because the relationship between the remaining charges Va and Vb and the third threshold Ta3 and Tb3 is Ta3−Va>Tb3−Vb, the battery A is charged with an increased charging current. In a case where, when the remaining charge Va exceeds the third threshold Ta3 at a certain timing, and the remaining charge Vb is still less than the third threshold Tb3, a control to change the ratio of charging currents can be performed at the certain timing. The third thresholds set in the present exemplary embodiment enable finer control of charging currents.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, these embodiments are not seen to be limiting. The scope of the following claims is to be accorded the broadest interpretation so as to encompass all such modifications and equivalent structures and functions.

This application claims the benefit of Japanese Patent Application No. 2022-071584, filed Apr. 25, 2022, which is hereby incorporated by reference herein in its entirety.

What is claimed is:
1. A radiographic imaging apparatus comprising:
a charging unit configured to input current to a plurality of batteries to charge the plurality of batteries; and
a current control unit configured to control the current to be input by the charging unit to each of the plurality of batteries, wherein the current control unit determines, based on a difference between a remaining charge of each of the plurality of batteries and a predetermined threshold, the current to be input by the charging unit to each of the plurality of batteries.

2. The radiographic imaging apparatus according to claim 1, wherein, for each of the plurality of batteries, the current control unit sets, as the predetermined threshold, a first threshold and a second threshold, wherein the first threshold indicates a limit of a remaining charge with which radiographic imaging can be performed for a predetermined number of images, and wherein the second threshold indicates an overcharging limit of a remaining charge.

3. The radiographic imaging apparatus according to claim 2, wherein the current control unit sets a third threshold at a value between the first threshold and the second threshold to each of the plurality of batteries.

4. The radiographic imaging apparatus according to claim 2, wherein in a case where the plurality of batteries includes at least one battery with a remaining charge less than the first threshold, the current control unit determines a battery to be charged from among the plurality of batteries having remaining charges less than the first threshold and causes the charging unit to charge the determined battery.

5. The radiographic imaging apparatus according to claim 4, wherein in a case where the plurality of batteries includes a plurality of batteries with remaining charges less than the first threshold, the current control unit causes the charging unit to charge a battery that has a smallest difference between the remaining charge and the first threshold.

6. The radiographic imaging apparatus according to claim 2, wherein in a case where the plurality of batteries includes a plurality of batteries with a remaining charge greater than or equal to the first threshold and less than the second threshold, the current control unit causes, based on a difference between the second threshold and the remaining charge of each of the plurality of batteries with a remaining charge greater than or equal to the first threshold and less than the second threshold, the charging unit to charge the plurality of batteries.

7. The radiographic imaging apparatus according to claim 6, wherein the current control unit causes the charging unit to charge a battery where the difference is large from among the plurality of batteries with remaining charges greater than or equal to the first threshold and less than the second threshold using a current larger in value than the battery where the difference is small.

8. The radiographic imaging apparatus according to claim 1, further comprising a measurement unit configured to measure the difference.

9. The radiographic imaging apparatus according to claim 1, further comprising:
an identification unit configured to identify materials the plurality of batteries are composed of,
wherein the current control unit determines a battery to be charged based on the identification.

10. The radiographic imaging apparatus according to claim 1, wherein the charging unit has a current dividing circuit configured to divide current and input the divided current to the plurality of batteries.

11. The radiographic imaging apparatus according to claim 10, wherein the charging unit has at least one charging circuit configured to supply current to the current dividing circuit.

12. A radiographic imaging system comprising:
a charging unit configured to input current to a plurality of batteries to charge the plurality of batteries;
a current control unit configured to control the current to be input by the charging unit to each of the plurality of batteries; and
a console configured to control the radiographic imaging apparatus,
wherein the current control unit determines, based on a difference between a remaining charge of each of the plurality of batteries and a predetermined threshold, the current to be input by the charging unit to each of the plurality of batteries.

13. A control apparatus of a radiographic imaging apparatus, the control apparatus comprising:
a current control unit configured to control current to be input to each of a plurality of batteries,
wherein the current control unit determines, based on a difference between a remaining charge of each of the plurality of batteries and a predetermined threshold, the current to be input to each of the plurality of batteries.

14. A control method of a radiographic imaging apparatus, the control method comprising:
determining, based on a difference between a remaining charge of each of the plurality of batteries and a predetermined threshold, current to be input to each of a plurality of batteries; and
controlling the current to be input to each of the plurality of batteries.

15. A non-transitory computer-readable storage medium storing a program for causing a computer to execute a method, the method comprising:
determining, based on a difference between a remaining charge of each of the plurality of batteries and a predetermined threshold, current to be input to each of a plurality of batteries; and
controlling the current to be input to each of the plurality of batteries.

* * * * *